US006432294B1

(12) United States Patent
Glass et al.

(10) Patent No.: US 6,432,294 B1
(45) Date of Patent: Aug. 13, 2002

(54) ELECTROCHEMICAL ACTIVATION OF ORGANIC DISULFIDES FOR ELECTROPHILIC SUBSTITUTION

(75) Inventors: Richard S. Glass, Tucson, AZ (US); Viatcheslav V. Jouikov, Cesson Sevigne (FR); Nina V. Bojkova, Tucson, AZ (US)

(73) Assignee: The University of Arizona, Tucson, AZ (US)

( * ) Notice: Subject to any disclaimer, the term of this patent is extended or adjusted under 35 U.S.C. 154(b) by 0 days.

(21) Appl. No.: 09/737,389

(22) Filed: Dec. 14, 2000

(51) Int. Cl.$^7$ .......................... C35B 3/02; C07D 213/00
(52) U.S. Cl. ...................... 205/426; 205/444; 546/173; 546/339
(58) Field of Search ................. 546/339, 193; 205/426, 444

(56) References Cited

U.S. PATENT DOCUMENTS

| | | |
|---|---|---|
| 1,940,757 A | 12/1933 | Lehmann et al. ................. 8/5 |
| 3,406,202 A | 10/1968 | Reifschneider et al. ...... 260/578 |
| 3,920,444 A | 11/1975 | Harrington et al. ............ 71/103 |
| 4,146,688 A | 3/1979 | Schwindt et al. ............ 521/159 |
| 4,324,920 A | 4/1982 | McKinnie et al. ............ 568/54 |
| RE31,771 E | 12/1984 | McKinnie et al. ............ 568/54 |
| 4,594,453 A | 6/1986 | Ranken et al. ............... 564/440 |
| 4,595,742 A | 6/1986 | Nalepa et al. ................ 528/64 |
| 4,670,597 A | 6/1987 | Ranken et al. ............... 564/440 |
| 4,670,598 A | 6/1987 | Davis ........................... 564/440 |
| 4,760,188 A | 7/1988 | Ranken et al. ............... 564/440 |
| 4,866,209 A | 9/1989 | Ranken et al. ............... 564/440 |
| 4,889,955 A | 12/1989 | Ranken ........................ 564/440 |
| 4,982,002 A | 1/1991 | McKinnie et al. .......... 564/440 |
| 5,534,036 A | 7/1996 | Junino et al. .................. 8/411 |
| 6,207,838 B1 * | 3/2000 | Glass et al. ................. 205/444 |

FOREIGN PATENT DOCUMENTS

| | | |
|---|---|---|
| EP | 0591059 | 4/1994 |
| JP | 5942346 | 3/1984 |

OTHER PUBLICATIONS

CAPLUS Abstract of Barton,et al., "New alkane functionalization reactions based on Gif–type chemistry in the presence of alkali metal salts", Tetrahedron Lett. (1993), vol. 34, No. 12, pp. 1871–1874.

Bewick et al., "Anodic Acetamidosulphenylation of Alkenes via Anodic Oxidation of Disulfides", J. Chem. Soc. Perkin Trans. vol. 1, 1985, pp. 1033–1038.

Bosscher, et al., "Electrophylic Methylthiolation and Arylthiolation of Aromatic Compounds with Thiosulphonates", Chemical Communications, 1971, pp. 1365.

Brintzinger et al., "Reaktionen mit Chlormethylschwefelchlorid, II. Mitteilung", Chemische Berichte, vol. 85, 1952, pp. 338–343 not translated.

Brintzinger et al., Synthesen mit Alkylschwefelchloriden (X. Mitteil.) über organische Schwefelchloride), Chemische Berichte vol. 87, 1954 pp. 325–330 not translated.

Brown et al., "Sulphides, Sulphoxides, and Sulphones derived from Salicylic Acids", Journal of the Chemical Society, Perkins Transactions, I, 1978, pp. 633–638.

Buess et al., "Derivatives of Sulfenic Acids. IV. The Reaction of 2,4–Dinitrobenzenesulfenyl Chloride with Aromatic Systems", J. Of Am. Chem. Soc. vol. 72, 1950, pp. 3529–3532.

pg,3

Capozzi, et al., "Methyl(bismethylthio)sulphonium salts and trimethylsilyl–suphenyl halides as synthons in organo–sulphur chemistry", Pure & Applied Chemistry, vol. 59, No. 8, 1987, pp. 989–992.

Capozzi, et al., "Reactions of Sulphenyl Chlorides and Disulphides in Acidic Media. Trapping of Alkyl(bisalkylthio)sulphonium Ion Intermediates" Journal of Chemical Society, Perkins Transactions, II, 1975, pp. 900–903.

Do, et al., "Electrophillic substitutions with the electrogenerated sulfenium cation R$^o$S$^+$", Tetrahedron Letters, vol. 39, 1998, pp. 4657–4658.

Dietrich, et al., "On the Determination of Redoxy Potentials of Highly Reactive Aromatic Mono– and Multications", J of Am. Chem. Soc., vol. 112, 1990, pp. 5142–5145.

Elothmani, et al., "Anodic Oxidation of Di–tert–butyl Disulfide: A Facile Method for the Preparation of N–tert–Butylamides", Chemical Society, Chemical Communications, 1993, pp. 715–717.

Farah, et al., "Alkylmercaptophenols by Sulfenylation of Phenols", Journal of Organic Chemistry, vol. 28, 1963, pp. 2807–2809.

Fujisawa et al., "Iron–Catalyzed Aromatic Sulfuration with Sulfenyl Clorides", Tetrahedron Letters, No. 49, 1968, pp. 5071–5074.

Fujisawa et al., "Ortho Effect of the Nitro Group on Iron–Catalyzed Aromatic Sulfuration With Substituted Benzenethiosulfenyl Chlorides", Tetrahedron Letters, No. 49, 1969, pp. 4291–4294.

Gilow et al., "Sulfenylation of Some Pyrroles and Indoles", Journal of Heterocyclic Chemistry, vol. 28, 1991 pp. 1025–1034.

Glass, et al., "Electrochemical Electrophilic Aromatic Methylthiation in Liquid SO$_2$", Tetrahedron Letters, vol. 40, (1999), pp. 6357–6358.

(List continued on next page.)

*Primary Examiner*—Bernard Dentz
(74) *Attorney, Agent, or Firm*—E. E. Spielman, Jr.

(57) ABSTRACT

Electrochemical oxidation of organic disulfides is conducted in an electrolytic solution containing an arene (e.g., anthracene, acenaphthylene, phenanthrene), and depending on the arene used and/or the product desired, an organic base (e.g., pyridine) to effect the synthesis of organothiated products in good yields.

35 Claims, No Drawings

OTHER PUBLICATIONS

Goux et al., "Liquid–phase alkylthiolation reaction of phenol by dimethyldisulfide over zeolites", Journal of Molecular Catalysis, vol. 89, 1994, pp. 383–390.

Grant et al., "Lewis Acid–catalysed Sulphenylations of Methylbenzenes by p–Chlorobenzenesulphenyl Chloride", Journal of Chemical Research (S), 1987, pp. 392–393.

Gray et al., "Pyrimidines. Part III.[1] Synthesis of Some 5–Alkythiopyrimidines", Journal of the Chemical Society (C), 1970, pp. 986–989.

Hojo et al., "Silica Gel as a Catalyst for the Condensations of Aromatic Compounds with RSCl, RSCH$_2$Cl, and S$_2$Cl$_2$", Synthetic Communications, vol. 5, No. 3, 1975, pp. 173–176.

Kharasch et al., "Derivatives of Sulfenic Acids. XV. A New Synthesis of Thiophenols", J. Of Organic Chem., vol. 19, 1954, pp. 1704–1707.

Ranken et al., "Alkylthio Aromatic Amines", Journal of Organic Chemistry, vol. 54, 1989, pp. 2985–2988.

Ranken et al., "Alkylthiolation of Phenols", Synthesis, 1984, pp. 117–119.

Robert D. Schuetz et al., "A New Synthesis of Thiophene– and Thianaphthenethiols", J of Organic Chem., vol. 27, 1962, pp. 1301–1304.

Verheijen et al., "Improved Synthesis of Benzo–1,4–dithiin and of Benzo–1,4–oxathiin", Synthesis, 1975, pp. 451–452.

Abstract of EP 0591059, issued 1994, (esp@cenet), 1 page.

Wragg, "The Synthesis of Alkyl p–Hydroxyphenyl Sulphides", Journal of the Chemical Society, 1964, pp. 5482–5483.

Yamamoto et al., "Anodic Oxidation of Diphenyl Disulfides for Preparation of Oligo(p–phenylene sulfide)s in Acid Media", Journal of Electrochemical Society, vol. 139, No. 9, 1992, pp. 2401–2406.

Yamamoto et al., "Electroactive Poly(Arylene Sulphide) Electro–Oxidative Polymerization of 3,5–Dimethylthiophenol" European Polymer Journal, vol. 28, No. 4, 1992, pp. 341–346.

Glass, Richard S., "Sulfur Radical Cations", Topics in Current Chemistry, vol. 205, Springer–Verlag Berlin Heidelberg, 1999, 87 pages.

Lund, Henning, "Electroorganic Preparations IV. Oxidation of aromatic hydrocarbons", Acta Chemica Scandinavica, 11, 1957, pp. 1323–1330.

Shang, et al., "The Electropreparation and Characterization of 9,10–dihydro–9,10–diphenyl–9,10–dipyridiniumanthracenc Diperchlorate: The product of the Anodic Pyridination of 9,10–diphenylanthracene", Electroanalytical Chemistry and Interfacial Electrochemistry, 54, 1974, pp. 305–311.

Weiss, et al., "A Convenient Synthesis of Methyl–bis[methylthio]sulfonium Hexachloroantimonate", Synthesis, 1976, pp. 323–324.

Dewar et al., "Electrophilic Addition to Olefins. I. The Stereochemistry of Addition of Deuterium Halides to Acenaphthylene", J. Am. Chem. Soc., 1963, vol. 85, pp. 2245–2248.

Dewar et al., "Long–range Coupling in the Nuclear Magnetic Resonance Spectra of Acenaphthene Derivatives", J. Am Chem. Soc., 1963, vol. 85, pp. 2704–2708.

Mueller, et al., "New Aspects of the Mechanism of Sulfenyl Chloride Additions to Olefins", J. Am. Chem. Soc., 1966, vol. 88, pp. 2866–2868.

Sternhell et al., "Proton Nuclear Magnetic Resonance Spectra of 1,2–disubstituted Acenaphthenes", J. Org. Chem., vol. 39, No. 25, 1974, pp. 3794–3796.

Olsen et al., "Addition Reactions and Stability of Arylsulfonly Thiocyanates", Acta Chem. Scand., B 29, 1975, No. 6, pp. 717–718.

Bewick et al., "Mechanism of Anodic Acetamidosulphenylation and Acetamidoselenation of Alkenes", J. Electroanal. Chem., 144, 1983, pp. 235–250.

* cited by examiner

ELECTROCHEMICAL ACTIVATION OF ORGANIC DISULFIDES FOR ELECTROPHILIC SUBSTITUTION

TECHNICAL FIELD

This invention relates to electrochemical oxidation of dihydrocarbyl disulfides in the presence of arenes, and to production of hydrocarbylthioarenes. This invention also relates to certain novel adducts and to the formation of these adducts.

BACKGROUND

Electrophilic thiation is typically accomplished by the use of a sulfenyl chloride, disulfide, or thiosulfonate, with a Lewis or Bronsted acid. Silica gel has been used to catalyze the reactions of sulfenyl chlorides with arenes, while zeolites have been used for catalysis of hydrocarbyl disulfide reactions with phenols.

A method has been reported for thiation using electrochemically generated sulfenium ion in dichloromethane, with low yields; see Do et al., *Tetrahedron Lett.*, 1998, 4657. The sulfur electrophile produced could effect substitution with highly activated phenols in 26–77% yield, but with the less activated anisoles the yields were only 11–35%.

Glass and Jouikov, in commonly-owned, copending application Ser. No. 09/302,908, filed on Apr. 30, 1999, now U.S. Pat. No. 6,207,838, describe electrooxidation of organic disulfides where thiation of arenes is accomplished in liquid $SO_2$. Although ahighly effective process, it does involve use of low temperatures and/or elevated pressures to keep the $SO_2$ in the liquid state during the process.

In both of the foregoing electrochemical methods, an electrophilic thiating agent is prepared electrochemically and then, in a subsequent step, it is added to the arene substrate in order to produce an organothiated arene. Such procedure requires that the electrophilic sulfur species persist until added to the arene. Although the Glass and Jouikov method gives higher yields than the Do, et al. method, the need for using low temperatures or high pressures to keep $SO_2$ in the liquid state is a shortcoming of that process.

It would be a considerable advantage if a way could be found for electrochemical organothiation to be achieved that avoids the need for low temperature and/or pressurized operation.

BRIEF SUMMARY OF THE INVENTION

This invention provides efficacious technology enabling production of organothiated arenes in good yield without the need for low temperature or high pressure. This invention provides for electrolytic oxidation of an organic disulfide ($R_2S_2$) in the presence of an organothiatable arene substrate in a liquid phase mixture. Organic electrochemical solvents in combination with a supporting electrolyte are used as the medium for the electrolytic oxidation, and thus the low temperature and/or elevated pressure conditions required for liquid $SO_2$ are avoided. By making the substrate one of the initial reactants during the electrolysis step, the problem of the instability of the electrophilic sulfur species formed by the anodic oxidation of the organic disulfide is averted.

Accordingly one of the embodiments of this invention is a process which comprises subjecting an organic disulfide in which the organic groups are primary or secondary organic groups to anodic oxidation in a solution formed from (i) an organothiatable arene containing only aromatic unsaturation, (ii) an organic electrochemical solvent, (iii) a dissolved supporting electrolyte, such that an organothiated arene is formed.

For some aromatic compounds, even controlled potential electrolysis results in overoxidation of the organothiated arene substrate and this can result in production of excessive amounts of unwanted by-products. Furthermore, the acid produced in the reaction can also result in production of excessive amounts of unwanted by-products. For example, when subjected to controlled anodic oxidation, arenes having a cycloolefinic moiety in the molecule such as acenaphthylene polymerize and form copious amounts of insoluble polymeric precipitates. However, pursuant to this invention, the problem of overoxidation and sensitivity to acid can be minimized, if not eliminated, by conducting the electrochemical reaction in the additional presence of an organic nucleophilic base, such as pyridine, with the resultant formation of novel adducts which are more resistant to oxidation, and which are highly useful as they can be subjected to eliminative aromatization in a subsequent reduction step, resulting in good yields of the desired thiated aromatic compounds. Thus, in the case of acenaphthylene, the inclusion of pyridine in the electrochemical reaction mixture overcame the polymer formation problem and resulted in the formation of an adduct which, upon electrochemical eliminative aromatization, gave 1-methylthioacenaphthylene in a yield of 76%.

Accordingly another of the embodiments of this invention is a process which comprises subjecting a dihydrocarbyl disulfide in which the organic groups are primary or secondary organic groups to anodic oxidation in a solution formed from (i) an organothiatable arene, (ii) an organic electrochemical solvent, (iii) a dissolved supporting electrolyte, and (iv) an organic nucleophilic base such that an adduct is formed in which the aromatic ring of a mononuclear arene or an aromatic ring of a polynuclear arene is dearomatized and is substituted on the dearomatized ring by an organothio group and a cationic organic base.

Such adducts are new compounds having good stability particularly towards oxidation. Thus a further embodiment of this invention is an adduct in which a cycloaliphatic ring is substituted by an organothio group, and by a cationic organic base, and wherein, optionally but preferably, the cycloaliphatic ring is attached, preferably fused, to at least one aromatic ring. The adducts of this invention can be recovered from the reaction mixture by conventional means for use, for example, as chemical intermediates. To illustrate, the adducts can be subjected to eliminative aromatization so as to form an organothiated arene.

Still another embodiment of this invention is a process which comprises:

A) subjecting an organic disulfide in which the organic groups are primary or secondary organic groups to anodic oxidation in a solution formed from (i) an organothiatable arene susceptible to overoxidation, (ii) an organic electrochemical solvent, (iii) a dissolved supporting electrolyte, and (iv) an organic nucleophilic base such that an adduct is formed in which the aromatic ring of a mononuclear arene or an aromatic ring of a polynuclear arene is dearomatized and is substituted on the dearomatized ring by an organothio group and a cationic organic base; and B) subjecting said adduct to eliminative aromatization such that an organothiated arene is formed.

Yet another embodiment of this invention is a process which comprises subjecting an organic disulfide in which the organic groups are primary or secondary organic groups to anodic oxidation:

A) in a solution formed from (i) an organothiatable arene having an oxidation potential at least about 150 mV higher than that of the organo disulfide, and (ii) a liquid organic dipolar aprotic solvent, such that organothiation occurs and an organothiated arene is produced; or B) in a solution formed from (i) an organothiatable arene having an oxidation potential that is lower, equal to, or less than 100 mV higher than that of the organo disulfide, (ii) a liquid organic dipolar aprotic solvent, and (iii) a nucleophilic organic base, such that an adduct is formed in which (a) an organothio group and (b) a molecule of the organic base are both bonded to a cycloaliphatic moiety derived from the arene; and subjecting said adduct to eliminative aromatization such that the organic base is removed from the adduct and the cycloaliphatic ring is aromatized whereby an organothiated arene is formed.

For example, in acetonitrile, dimethyl disulfide shows an irreversible first oxidation peak at 1.05 V vs Ag/O.1M AgNO$_3$ in acetonitrile reference electrode using the technique of cyclic voltimetry. The oxidation peak of anthracene is about 400 mV more positive than that for dimethyl disulfide. Consequently, pursuant to this invention, dimethyl disulfide can be selectively oxidized electrolytically in the presence of anthracene to produce the organothiated product, 9-methylthioanthracene, in very good yield.

These and other embodiments and features of this invention will be still further apparent from the ensuing description and appended claims.

FURTHER DETAILED DESCRIPTION

As indicated above, in the practice of this invention some arenes can be electrochemically organothiated in one step to produce an organothiated arene, Ar(—SR), where n is typically 1 but can be 2. A good illustration of this is the controlled electrochemical oxidation of dimethyl disulfide in the presence of anthracene as described in Example 1 wherein without use of a nucleophilic organic base, 9-methylthioanthracene was produced in 74% yield, along with an 8% yield of 9,10-di(methylthio)anthracene. While some overoxidation occurred, the extent of overoxidation was not excessive. On the other hand, with other arenes it may be desirable, if not essential to perform the operation in two steps whereby in the first step the electrochemical organothiation is conducted in the presence of a nucleophilic base so that an adduct of this invention is formed. In the second step the adduct is subjected to eliminative aromatization such that the organic base is removed from the adduct and the cycloaliphatic ring is aromatized whereby an organothiated arene is formed. Thus in any case where it is desired to form an organothiated arene (instead of an adduct of this invention as the end product), and the behavior of the initial arene towards anodic oxidation under suitably controlled conditions is not known, it is desirable to perform a few preliminary tests under conditions such as set forth in the Examples hereinafter to determine whether a one step or a two-step process should be used.

As an example of the benefits that can be realized by use of the two-step procedure, controlled potential electrolysis of dimethyl disulfide in the presence of acenaphthylene in the absence of an organic nucleophilic base resulted in copious polymer formation. But when the same electrolysis procedure was conducted in the additional presence of pyridine, an oxidation-resistant adduct of this invention formed which on eliminative aromatization in the second step resulted in the production of 1-methylthioacenaphthylene in 76% yield using electrochemical reductive elimination.

Anthracene does not form a pyridinium adduct under these conditions, and thus use of an organic nucleophilic base is not of help in this instance. It is believed that the inhibition of adduct formation in this case may be explained by the lack of formation of thiiranium salts which precede the adduct formation.

Organic Thiating Agent

The organic disulfides utilized in the practice of this invention can be represented by the formula R-S-S-R where R is an organic group. Although there are two organic groups in the molecule, when the organic groups are the same, such compounds may be named, for example, as methyl disulfide instead of dimethyl disulfide. The organic groups of the organic disulfides utilized in the practice of this invention can be hydrocarbyl groups (i.e., the organic groups consist of carbon and hydrogen), or they can be functionally-substituted hydrocarbyl groups wherein the substituent(s) on the hydrocarbyl group do not interfere with the formation of the organo thiating agent or the reactions involved in forming the organothio arene product being produced. Tertiary hydrocarbyl disulfides are not desired as organic disulfides in the practice of this invention because they have been reported not to generate thiating agents; see Elothmani et al., J Chem. Soc., Chem. Comm., 1993, 715. Because alkenes are known to react with thiating agents, nonaromatic unsaturation is also undesirable in the organic disulfide. Therefore it is preferable that the organic disulfide used is a hydrocarbyl disulfide in which the hydrocarbyl groups are free of non-aromatic unsaturation.

The hydrocarbyl groups of the disulfides used in the practice of this invention can be primary or secondary aliphatic, cycloaliphatic, or aromatic hydrocarbyl groups which are free of non-aromatic unsaturation. Preferably, the hydrocarbyl groups will each contain up to about 18 carbon atoms, and more preferably, up to about 8 carbon atoms. Of the dihydrocarbyl disulfides, preferred are the primary alkyl disulfides in which the alkyl groups can be the same or different and can be linear or branched.

The organic disulfides in which the organic groups contain one or more innocuous functional substituents are compounds in which the substituents are, for example, halogen atoms, alkoxy groups, aryloxy groups, nitro groups, esterified carboxyl groups, nitrile groups, heterocyclic groups in which the heteroatom(s) is/are oxygen and the like. Examples of suitable organic disulfides include dimethyl disulfide, diethyl disulfide, bis(2-hydroxyethyl) disulfide, dipropyl disulfide, bis(3-carboxypropyl) disulfide, diisopropyl disulfide, di-n-butyl disulfide, di-sec-butyl disulfide, bis(2,2,4,4-tetramethylcyclobutyl) disulfide, bis (heptafluorocyclobutyl) disulfide, dipentyl disulfide, dicyclopentyl disulfide, dicyclohexyl disulfide, dicyclooctyl disulfide, di-o-tolyl disulfide, di-p-tolyl disulfide, bis(3-nitrophenyl) disulfide, di-1-naphthyl disulfide, di-2-naphthyl disulfide, and the like. A preferred group of dihydrocarbyl disulfides are primary hydrocarbyl disulfides, RCH$_2$—S—S—CH$_2$R, where R is a hydrocarbyl group, preferably having up to about 17 carbon atoms, more preferably up to about 7 carbon atoms, and in which there is no non-aromatic unsaturation. Particularly preferred dihydrocarbyl disulfides are dimethyl disulfide and diethyl disulfide, especially dimethyl disulfide.

Arene Substrate

A wide variety of aromatic compounds are suitable as organothiatable substrates, provided that the site to be organothiated has a hydrogen atom as its substituent, and that other constituents, if any, present in the compound to not interfere with the desired reaction(s). The aromatic compounds may be heterocyclic compounds such as those containing oxygen or sulfur, or homocyclic compounds. In either case, the aromatic compounds may be mononuclear (i.e., single ring compounds) or polynuclear. Aromatic compounds with fused ring systems are preferred. Examples of homocyclic aromatic compounds deemed suitable for use in the practice of this invention include benzene, naphthalene, anthracene, phenanthrene, acenaphthene, acenaphthylene, indene, isoindene, fluorene, chrysene, pyrene, triphenylene, toluene, xylene, biphenyl and similar compounds. Heterocyclic aromatic compounds deemed suitable include thionaphthalene, xanthene, furan, benzofuran, isobenzofuran, and the like. Those arenes most preferred are anthracene, phenanthrene, and acenaphthylene.

Examples of substituents (other than hydrogen atoms) which may be present on the aromatic ring include, but are not limited to, hydroxy groups, hydrocarbyl groups, and hydocarbyloxy groups. Aromatic rings containing as fuictional substituents only deactivating substituents are not expected to react with an organothiating agent. Deactivating substituents, such as nitro groups and carboxyl groups, may be present under one of the following two conditions: first, when an activating substituent is also present on the aromatic ring to be organothiated, as in, for example, p-nitrophenol or 2-methyl-3-nitronaphthalene; second, when reaction with a different aromatic ring is desired, for a compound with two or more aromatic rings, as in, for example, 3-nitrofluorene. Substituted homocyclic aromatic compounds that may be used include methoxybenzene, thioanisole, acenaphthalene, 2-isopentoxynaphthalene, 7-isopropyl-1-methylphenanthrene, 3-methylindene, 1,2-diphenylindene, 5,6-dimethylchrysene, 2,7-dimethylpyrene, 1-acetylpyrene, 1,3-dimethylanthracene, 9,10-dibenzylanthracene, 4,4'-dimethoxybiphenyl, 2,4'-diethoxy-3,3'-dimethylbiphenyl, and the like. Substituted heterocyclic aromatic compounds include, for example, 2-octylthiophene, 9-phenylxanthene, 2-benzoylbenzofuran, 2-tert-butylfuran, 2,5-dimethoxyfuran, and similar compounds. Typically, the aromatic compound used as the substrate will contain up to about 40 carbon atoms.

Organic Nucleophilic Bases

Although pyridine is the preferred organic nucleophilic base for use in those embodiments where a two-step is to carried out, other compounds of this type can be used. A few examples include 2-picoline, 3-picoline, 4-picoline, 2,4-lutidine, 2,6-lutidine, 3,4-lutidine, 3-ethylpyrine, 4-ethylpyridine, aldehydine, α-collidine, β-collidine, β-parvoline, 4-methoxypyridine, quinoline, lepidine, 8-methylquinoline, 5,8-dimethylquinoline, β-cytisolidine, and the like.

Proportions

Variations are possible in the proportions in which the disulfide and the arene substrate are used in the organothiation reaction. Each mole of organic disulfide has in theory the capability of organothiating two organothiatable sites in one mole of the substrate. Thus, in situations where there is only one organothiatable site in the substrate, or where the substrate has more than one organothiatable site and all such sites are to be organothiated, the relative proportions of the disulfide and of the substrate can be widely varied from a stoichiometric deficiency of the disulfide to a stoichiometric excess of the disulfide relative to the substrate. To minimize the amounts of unreacted materials to be separated from the organothiated product (when such separation is desired), the organothiating reagent and such substrate are preferably mixed together in approximately stoichiometric proportions so that the conversion of both reactants to desired product is essentially complete.

When the substrate contains a plurality of organothiatable sites, but less than all are to be organothiated, it is desirable to employ an amount of the disulfide that is somewhat less than, equivalent to, or only slightly more than the stoichiometric amount required to effect the extent of organothiation desired. For example, when more than one organothiatable site is present in the substrate, and mono-organothiation is desired, amounts of organic disulfide below one mole per mole of substrate can be used, although it is usually preferable to use approximately one mole or a small excess (e.g., up to about 1.5 moles) of the disulfide per mole of such substrate. But when more than two organothiatable sites are present in the substrate, and di-organothiation is desired, the preferred amount of disulfide is approximately 2 to about 2.5 moles per mole of such substrate. However, if using less than two moles of disulfide in such a situation, at least an amount above one mole of the disulfide should be used per mole of the such substrate to ensure that at least some di-organothiated product will be produced. Thus in general, when the number of organothiatable sites is greater than the number of sites that are intended to be organothiated, amounts of disulfide used should be such as to provide a sufficient conversion to the desired product without producing an undesirable amount of unwanted by-products. However, while not a preferred embodiment of this invention, under some circumstances, a mixture of products may be desired, and in such case the proportions are adjusted accordingly. The most preferred proportion used is about one mole of organic disulfide per mole of sites to be organothiated.

When an organic nucleophilic base is used, it will typically be used in proportions at least equivalent to the number of moles of arene present in the mixture being subjected to anodic oxidation. Preferably the base will be present in an amount in the range of about I to about 2 moles per mole of arene.

Solvent

A wide variety of known electrochemical solvents can be employed in the practice of the electrochemical oxidation of this invention. For a discussion of such solvents, see for example, H. Lund and M. Baizer, *Organic Electrochemistry; an Introduction and Guide*, Marcel Dekker pubs., New York, 1991. Among suitable solvents are polar chlorohydrocarbons such as methylene chloride and polar aprotic solvents such as acetonitrile. Preferred are inert polar solvents, which preferably have an electric dipole moment of at least about $1\mu$ as measured in the gaseous state or in benzene or 1,4-dioxane. See, for example, A. L. McClellan, *Tables of Experimental Dipole Moments*, 1963.

Preferred solvents are liquid organic polar solvents which are suitable for sustaining the electrolysis reaction. These include organic compounds with carbon groups having between 2 and about 10 carbon atoms, more preferably those having 2 to about 5 carbon atoms. Examples of suitable dipolar aprotic solvents with high polarity (e.g., with dipole moments of at least about $2.2\mu$ and preferably at least about $3\mu$) include but are not limited to acetonitrile, propionitrile, benzonitrile, N,N-dimethyl formamide, N,N-diethyl formamide, dimethyl sulfoxide, sulfolane, N,N-dimethyl acetamide, N,N-diethyl acetamide, propylene carbonate and the like. Of such solvents, acetonitrile is most preferred.

Supporting Electrolvte

Various known supporting electrolytes can be used in the electrochemical oxidation process. These include appropriate alkali metal salts that are soluble in the solvent used, such as alkali metal perchlorates and alkali metal triflates. Quaternary ammonium salts can also be used. In order to properly support current flow in the solution, the supporting electrolyte is typically present in the solution at least as a 50 millimolar solution, and preferably as an approximately 0.1 molar solution. Further details concerning supporting electrolytes and their use are known and reported in the literature. See for example, H. Lund and M. Baizer, *Organic Electrochemistry; an Introduction and Guide*, Marcel Dekker pubs., New York, 1991.

Reaction Conditions for Anodic Oxidation

The electrochemical process of this invention can be readily conducted in a two compartment electrochemical cell using as a working electrode (anode) a cylinder of platinum gauze, and as an auxiliary electrode (cathode) an aluminum cylinder. A silver wire can serve as the reference electrode. The applied potential is typically in the range of about +0.7 to about +1.2 volts. For further discussion of electrochemical cells and techniques, see, for example, A. Fry, *Synthetic Organic Electrochemistry*, John Wiley and Sons, New York, 1989.

Typically, the electrochemical process is initiated at about room temperature although higher or lower temperature conditions can be employed if desired. Pressure normally is of no consequence in this reaction, and thus the reaction is usually performed at the atmospheric pressure prevailing at the time of the operation.

Eliminative Aromatization

Preferred adducts of this invention may be represented by the formula:

RS-CY-CX-$^{\oplus}$NB where RS is an organothio group having up to about 18 carbon atoms, and more preferably, up to about 8 carbon atoms, and in which organic portion, R, is a primary or secondary organic group, preferably a primary or secondary hydrocarbyl group, more preferably a primary alkyl group, still more preferably a methyl or ethyl group, and most preferably a methyl group; CY-CX is a 5 or 6-membered cycloaliphatic group having either 5 carbon atoms or 6 carbon atoms in a homocyclic ring system, or a 6-membered ring having 5 carbon atoms and one oxygen, nitrogen, or sulfur hetero atom; and $^{\oplus}$NB is an organic base.

When it is desired, as in a two-step processes of this invention, to convert such an adduct into an organothioarene RS-Ar where RS is as defined above, and Ar is an univalent aromatic group derived from an arene by loss of a ring hydrogen atom, the adduct is subjected to an eliminative aromatization step. This can be conducted either non-electrochemically or electrochemically. In a non-electrochemical eliminative aromatization step, the adduct is treated with a suitable base such as an alkali metal alkoxide in an anhydrous alcohol medium or with an organic base such as an amidine in an inert medium such as an ether. Use of sodium methoxide in anhydrous methanol, or either 1,5-diazabicyclo[4.3.0]non-5-ene (DBN) or 1,8-diazabicyclo[5.4.0]undec-7-ene (DBU) in tetrahydrofuran, serve as typical examples of such basic treating agents.

The following examples are presented for purposes of illustration and are not intended to impose limitations on the scope of this invention. In these experiments $^1$H and $^{13}$C NMR spectra were recorded in the solvent indicated with 0.5% TMS as internal standard using a Bruker AM 250 spectrometer at 250.13 and 62.9 MHz, respectively. EI-MS were done using a Hewlett Packard HP5988A mass spectrometer. FAB mass spectra were measured using a JEOL XH110A instrument. Elemental analysis was performed by Desert Analytics, Tucson, Ariz. Thick layer chromatography was done using Analtech Uniplate GF 2000 silica gel plates. Column chromatographywas accomplished with silicagel (75–125 j.1m) supplied by Analtech, Newark, Del.

The electrochemical oxidations were done using three electrodes in a two-compartment cell and a PAR-362 potentiostat. A Pt gauze (3×5 cm) was used as the anode and Al foil (5×10 cm) as the cathode.

EXAMPLE 1

Electrolysis of $Me_2S_2$ in the Presence of Anthracene

A solution of $Me_2S_2$ (310 mg, 3.3 mmol) and anthracene (534 mg, 3.0 mmol) dissolved in anhydrous acetonitrile (25 mL) containing $NaClO_4$ (850 mg, 7 mmol) was electrooxidized at +0.85V vs Ag/0.1M $AgNO_3$ in acetonitrile, but other types of reference electrodes may be used as well. After an amount of electricity corresponding to 2 F/mol of $Me_2S_2$ was passed the current dropped to approximately 10% of its initial value and the electrolysis was stopped. The solvent was removed by evaporation in vacuo and the residue was extracted with cold distilled water to remove $NaClO_4$. The organic residue was then chromatographed on silica gel plates using hexanes: $CH_2Cl_2$ (1:1) as eluent. The fractions collected were:

1) 9-Methylthioanthracene, 494 mg (74% yield), mp 63–64° C. (identical with authentic compound by $^1$H NMR and mass spectroscopy and mmp);
2) 9,10-Di(methylthio)anthracene, 85.9 mg (11% yield), mp 161–162° C. (identical with authentic compound by $^1$H NMR and mass spectroscopy and mmp);
3) A dimer, tentatively identified as the 10,10'-dimer of 9-methylthioanthracene, 60 mg (5% yield): $^1$H NMR $(CDCl_3)\delta$ 2.39 (s,6H), 7.45 (m, 4H), 7.62 (m, 4H), 8.0 (m, 4H), 8.9 (d, 4H, J=8.9Hz); MS (EI) 446, 431, 384, 352, 286, 271, 209, 175, 166, 111;
4) Bis(dimethylthio)ketal of 9,10-anthraquinone, ca. 13 mg of crude product (1–3% yield): $^1$H NMR $(CDCl_3)\delta$ 2.18 (s, 12H), 7.68 (m, 4H); 8.58 (m, 4H); MS (EI) 364, 349, 334, 317, 270, 240, 176, 111, 104;
5) Anthraquinone, 59 mg (10% yield), mp 284–285° C. (identical with authentic compound).

The formulas for ketal and the dimer are given in FIGS. 1 and 2 respectively.

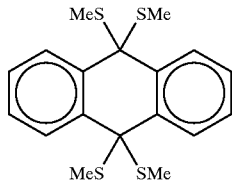

FIG. 1

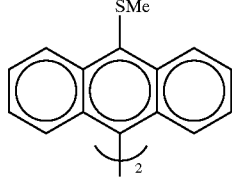

FIG. 2

EXAMPLE 2

Electrolysis of $Me_2S_2$ in the Presence of Phenanthrene and Pyridine

The electrolysis was carried out in a two compartment cell of 30 mL volume separated by a sintered glass diaphragm.

The working electrode was a Pt gauze cylinder (1.2 cm diam., 4 cm length), the counter electrode Al foil (30 cm² area), and the reference electrode Ag/0.1 M AgNO₃ in acetonitrile. A typical solution contained phenanthrene (6.5 mmol), Me₂S₂ (0.30g, 3.2 mmol), pyridine (1.2 g, 15 mmol) and NaClO₄ (1.5 g, 10 mmol) dissolved in acetonitrile (30 mL). The electrolysis was carried out at an applied potential of 1.0–1.2 V until the amount of electricity corresponding to 2 F/mol was passed. The anolyte was rotary evaporated and the residue extracted with hexane to leave a solid which was extracted with CH2Cl₂. The organic extracts were combined, washed with O.1M aqueous HCl solution, dried, rotary evaporated and the residue purified by column chromatography when necessary. The product collected was as follows:

6) Pyridinium adduct from methylthiation of phenanthrene, 46% yield: $^1$H NMR [(CD₃)₂CO] δ 2.26 (s, 3H, SMe), 4.99 (d, 1H, J=2.17 Hz), 6.7 (d, 1H, J=2.17 Hz), 7.36 (m, 2H), 7.52 (m, 2H), 7.76 (m, 2H), 8.13 (d, 2H, J=7.5 Hz) 8.16 (d, 1H, J=7.5 Hz), Hz), 8.25 (d, 1H, J=7.6 Hz) 8.63 (t, 1H, J=7.5 Hz), 8.86 (d, 2H, J=6.8 Hz); $^{13}$C NMR [(CD₃)₂CO] δ 15.1,50.7, 72.1, 125.7, 129.6, 130.2, 130.4, 130.5, 131.2, 133.0, 135.9, 144.4, 147.6; FAB-MS m/z 304.

EXAMPLE 3

Electrolysis of Me₂S₂ in the Presence of Acenaphthylene and Pyridine 5 The electrolysis was carried out as in Example 2 except using acenaphthylene (4.4 g, 29 mmol), Me₂S₂ (1.21 g, 13 mmol), pyridine (4.0 g, 50 mmol) and 0.05 M NaClO₄ in acetonitrile (30 mL). The electrolysis was carried out at an applied potential of 0.8–1.1 V until the amount of electricity corresponding to 2 F/mol was passed. The anolyte was rotary evaporated and the residue extracted repeatedly with benzene until the extracts were essentially colorless. The combined extracts were washed with water (20 mL). The organic extracts were dried, rotary evaporated, and the residue recrystallized from CH₂Cl₂ —diethyl ether.

7) Pyridinium adduct from methylthiation of acenaphthylene, 87% yield: $^1$H NMR [(CD3)₂ CO] δ 2.07 (s, 3H), 5.33 (d, 1H, J=3.3, Hz), 7.07 (d, IH, J=3.3 Hz), 7.6 (d, 1H, J=6.8 Hz), 7.7 (m, 2H), 7.8 (d, 1H, J=7.0 Hz), 8.00 (d, $^1$H, J=8.2 Hz), 8.09 (d, 1H, J=8.0 Hz), 8.36 (t, 2H, J=7.0 Hz), 8.85 (t, 1H, J=7.7 Hz), 9.18 (m, 2H); $^{13}$C [(CD3)₂CO)] δ 12.1, 58.0, 82.3, 122.6, 123.5, 125.9, 128.1, 129.8, 130.2, 130.4, 132.2, 137.7, 138.6, 139.7,144.7, 148.1; FAB-MS m/z 278.

The structures of the adducts 6 and 7, shown in FIGS. 3 and 4 respectively, were confirmed by preparing these same adducts chemically by the reaction of [(MeS)₂SMe]SbCl₆ and pyridine with phenanthrene or acenaphthylene in CH₂Cl₂. The structures of these adducts, including their stereochemistry, was determined spectroscopically. See in this connection Dewar, et al. J. Am. Chem. Soc. 1963, 85, 2245; Ibid., 1963, 85, 2704; Mueller, et al. J. Am. Chem. Soc. 1966, 88, 2866; Sternhell, et al. J. Org. Chem. 1974, 39, 3794; and Olsen, et al. 25 Acta Chem. Scand. 1975, B29, 717.

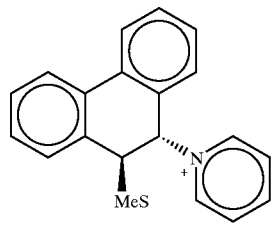

FIG. 3

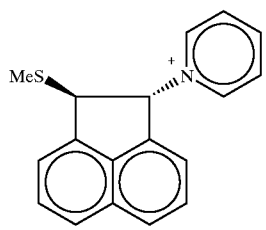

FIG. 4

EXAMPLE 4

Eliminative Aromatization of Pyridinium Adduct from Methylthiation of Phenanthrene (Adduct of FIG. 3)

Dehydropyridination of this adduct was conducted non-electrochemically. A solution of NaOMe was prepared by adding sodium metal (18 mg, 0.78 mmol) to anhydrous MeOH (1.0 mL). This solution was added to a solution of the adduct (66 mg, 0.10 mmol) dissolved in anhydrous THF (1.0 mL) at room temperature. After 1 h a precipitate formed, the solvents were rotary evaporated and water (5 mL) was added. The mixture was extracted with CH₂Cl₂ (3×10 mL) and the combined extracts washed with 5% aqueous HCl solution and then brine. The organic phase was separated, dried (anhyd MgSO₄), filtered, concentrated by rotary evaporation and chromatographed on silica gel (eluting with CH₂Cl₂/pentane) to give pure 9-methylthiophenanthrene (14 mg, 61% yield).

EXAMPLE 5

Eliminative Aromatization of Pyridinium Adduct from Methylthiation of Acenaphthylene (Adduct of FIG. 4)

Dehydropyridination of this adduct was conducted both non-electrochemically and electrochemically. Treatment of the adduct (160 mg, 0.42 mmol), with 1,8-diazabicyclo [5.4.0]undec-7-ene (DBU) (109 mg, 0.70 mmol) in anhydrous THF (20.0 mL) resulted in the formation of a deep red solution. After 18 h at room temperature the mixture was rotary evaporated and the residue dissolved in CHCl₃, and then chromatographed through a short silica gel column to give 1-methylthioacenaphthylene (64 mg, 76% yield): $^1$H NMR (CDCl₃)δ 2.62 (s, 3H), 6.58 (s, 1H), 7.44 (m, 2H), 7.52 m, 1H), 7.63 (m, 1H), 7.70(d, 1H, J=6.8 Hz), 7.80(d, 1H, J=8.1Hz); $^{13}$CNMR(CDCl₃)δ 15.4, 119.6, 121.0, 121.7, 125.2, 127.3, 127.9, 128.0, 129.1, 138.7, 139.7, 141.1; HR MS(FAB)calcd for C₁₃H₁₀S: 198.0503, Found: 198.0506.

Electrochemical dehydropyridination was achieved by reducing adduct (226 mg, 0.6 mmol) in acetonitrile containing 0.01M Et₄NClO₄ as supporting electrolyte in a two 1L compartment cell with Pt gauze electrode. After approximately 1.3 F/mol of electricity was passed, the acetonitrile was evaporated and the residue was extracted with CH₂Cl₂.

The extracts were washed through a short column of silica gel (1×0.5 in.) and then chromatographed on a large silica gel column (4×0.5 in.) eluting with $CH_2Cl_2$: hexanes (2: 1) to give 0.28 mmol of 1-methylthioacenaphthylene (47% yield).

As noted above, the adducts of Examples 2 and 3 were also prepared by reaction of phenanthrene and acenaphthylene with $[(MeS)_2SMe]SbCl_6$ and pyridine. These preparations are set forth in Examples 6 and 7.

EXAMPLE 6

Reaction of Phenanthrene with $[(MeS)_2SMe]SbCl_6$ and Pyridine

A solution of phenanthrene (546 mg, 3.07 mmol) dissolved in anhydrous $CH_2Cl_2$ (1.0 mL) was added to a solution of $[(MeS)_2SMe]SbCl_6$ (1.38 g, 2.90 mmol) dissolved in anhydrous $CH_2Cl_2$ (18 mL) with stirring. The color of the solution changed to deep purple. A solution of pyridine (246 mg, 3.11 mmol) in $CH_2Cl_2$ (1.0 mL) was added after 1 min. whereupon the purple color disappeared and a yellow precipitate formed. The mixture was stirred at room temperature for 23 h. The mixture was then filtered and the orange precipitate washed with $CH_2Cl_2$. After drying in vacuo a pyridinium adduct corresponding to that of Example 2 (depicted in FIG. 3) was obtained as orange crystals (1.1 g, 59% yield): mp 124–125° C. 125° C. (d); IR (KBr) 3121, 3073, 2917, 1702, 1623, 1477, 1434, 1358, 1249, 1219, 1165, 1123, 1053, 1024, 961, 749, 706, 673, 626, $cm^{-1}$; $^1H$ NMR $[(CD_3)_2CO]$ δ 2.20 (s, 3H), 4.94 (d, 1H, J=1.3 Hz), 6.69 (d, 1H, J=1.3 Hz), 7.36 (m, 2H), 7.54 (m, 2H), 7.77 (m, 2H), 8.15 (m, 3H), 8.25 (d, 1H, J=7.6 Hz), 8.65 (t, 1H, J=7.7 Hz), 8.89 (d, 2H, J=5.8 Hz); $^{13}C$ NMR $[(CD_3)_2 CO]$ δ 15.0, 50.8, 72.3, 125.7, 125.9, 127.2, 129.6, 130.2, 130.4, 130.5, 131.1, 131.5, 132.6, 132.8; 133.0, 135.6, 144.3, 147.6; HR MS (FAB). Calcd for $C_{20}H_{18}NS$: 304.1160. Found: 304.1150.

EXAMPLE 7

Reaction of acenaphthylene with $[MeS)_2 SMe]SbCl_6$ and Pyridine

The reaction was carried out as in Example 6 except using acenaphthylene (146 mg, 0.96 mmol) and anhydrous pyridine (164 mg, 2.08 mmol) dissolved in $CH_2Cl_2$ (2 mL) added to $[(MeS)_2 SMe] SbCl_6$ (446 g, 0.935 mmol) dissolved in $CH_2Cl_2$ (8 mL). After 20 h at temperature the mixture was concentrated on a rotary evaporator and analyzed by $^1H$ NMR spectroscopy showing acenaphthylene (0.5 mmol), 48% conversion) and 7 (0.4 mmol, 86% yield). This residue was purified by column chromatography on silica gel eluting with $CH_2Cl_2$ to give the adduct corresponding to that of Example 3 (depicted in FIG. 4) as its $SbCl_6$ salt as a red solid: 162 mg (58% yield): $^1H$ and $^{13}C$ NMR spectra and FAB-MS are identical to the adduct of Example 3, $ClO_4$; m.p 164–166° C. (d); IR (KBr) 3125, 3078, 2917, 2359, 2336, 1699, 1623, 1484, 1424, 1358, 1259, 1202, 1146, 974, 825, 789, 752, 706, 679. Calcd for $Cl_{18}H_{16}Cl_6NSSb$: C, 35.28; H 2.61; Cl, 34.72. Found: C, 35.32; H, 2.62; Cl, 35.54.

If desired other adducts of this invention can be prepared chemically as in Examples 6 and 7 by replacing $[MeS)_2 SMe]SbCl_6$ with analogs in which the methyl group is replaced by another hydrocarbyl group, such as ethyl, butyl, phenyl, tolyl, cyclopentyl, cyclohexyl, methylcyclopentyl, benzyl, etc., or replacing the phenanthrene and the acenaphthylene with other arenes such as referred to above, or both.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure.

Each and every patent or other publication referred to in any portion of this specification is incorporated into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises subjecting an organic disulfide in which the organic groups are primary or secondary organic groups to anodic oxidation in a solution formed from (i) an organothiatable arene containing only aromatic unsaturation, (ii) an organic electrochemical solvent, (iii) a dissolved supporting electrolyte, such that an organothiated product is formed from the arene.

2. A process according to claim 1 wherein said arene is a homocyclic arene.

3. A process according to claim 2 wherein said homocyclic arene is a fused ring arene.

4. A process according to claim 1 wherein said arene is anthracene and wherein said organothiated product comprises an organothioanthracene.

5. A process according to claim 1 wherein said solution is additionally formed from an organic nucleophilic base.

6. A process according to claim 5 wherein said base is pyridine or a ring-substituted pyridine.

7. A process according to claim 5 wherein said arene is phenanthrene and wherein said organothiated product comprises an adduct in which the central ring is dearomatized and is substituted by an organothio group and a cationic organic base.

8. A process according to claim 5 wherein said arene is acenaphthylene and wherein said organothiated product comprises an adduct in which the ethylene bridge is deprotonated and is substituted by an organothio group and a cationic organic base.

9. A process which comprises subjecting a dihydrocarbyl disulfide in which the organic groups are primary or secondary organic groups to anodic oxidation in a solution formed from (i) an organothiatable arene, (ii) an organic electrochemical solvent, (iii) a dissolved supporting electrolyte, and (iv) an organic nucleophilic base such that an adduct is formed in which the aromatic ring of a mononuclear arene or an aromatic ring of a polynuclear arene is dearomatized and is substituted on the dearomatized ring by an organothio group and a cationic organic base.

10. A process according to claim 9 wherein said arene is a homocyclic arene.

11. A process according to claim 10 wherein said homocyclic arene is a fused ring arene.

12. A process according to claim 9 wherein said base is pyridine or a ring-substituted pyridine.

13. A process according to claim 9 wherein said arene is a homocyclic fused ring arene, and wherein said base is pyridine or a ring-substituted pyridine.

14. An adduct in which the aromatic ring of a mononuclear arene or an aromatic ring of a polynuclear arene is dearomatized into a cycloaliphatic ring, said cycloaliphatic ring being substituted by an organothio group and a cationic organic base.

15. An adduct according to claim 14 wherein said adduct is a homocyclic adduct.

16. An adduct according to claim 15 wherein said homocyclic adduct is a fused ring adduct.

17. An adduct according to claim 14 wherein said cationic organic base is cationic pyridine or a cationic ring-substituted pyridine.

18. An adduct according to claim 14 wherein said adduct is a homocyclic fused ring adduct, and wherein said cationic organic base is cationic pyridine or a cationic ring-substituted pyridine.

19. An adduct according to claim 14 of the formula:

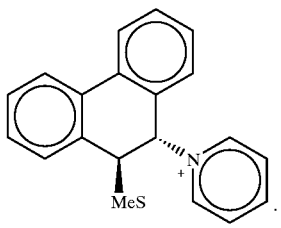

20. An adduct according to claim 14 of the formula:

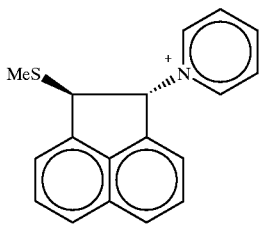

21. A process which comprises:
A) subjecting an organic disulfide in which the organic groups are primary or secondary organic groups to anodic oxidation in a solution formed from (i) an organothiatable arene susceptible to overoxidation, (ii) an organic electrochemical solvent, (iii) a dissolved supporting electrolyte, and (iv) an organic nucleophilic base such that an adduct is formed in which the aromatic ring of a mononuclear arene or an aromatic ring of a polynuclear arene is dearomatized and is substituted on the dearomatized ring by an organothio group and a cationic organic base; and
B) subjecting said adduct to eliminative aromatization such that an organothiated arene is formed.

22. A process according to claim 21 wherein the eliminative aromatization is conducted non-electrochemically.

23. A process according to claim 21 wherein said arene is a homocyclic arene.

24. A process according to claim 23 wherein said homocyclic arene is a fused ring arene.

25. A process according to claim 21 wherein said base is pyridine or a ring-substituted pyridine.

26. A process according to claim 21 wherein said arene is a homocyclic fused ring arene, and wherein said base is pyridine or a ring-substituted pyridine.

27. A process which comprises subjecting an organic disulfide in which the organic groups are primary or secondary organic groups to anodic oxidation:
A) in a solution formed from (i) an organothiatable arene having an oxidation potential at least about 150 mV higher than that of the organo disulfide, (ii) an organic electrochemical solvent, and (iii) a dissolved supporting electrolyte, such that organothiation occurs and an organothiated arene is produced; or
B) in a solution formed from (i) an organothiatable arene having an oxidation potential that is lower, equal to or less than 100 mV higher than that of the organo disulfide, (ii) an organic electrochemical solvent, (iii) a dissolved supporting electrolyte, and (iv) a nucleophilic organic base, such that an adduct is formed in which (a) an organothio group and (b) a cationic molecule of the organic base are both bonded to a cycloaliphatic moiety derived from the arene; and subjecting said adduct to eliminative aromatization such that an organothiated arene is formed.

28. A process according to claim 27 wherein the eliminative aromatization is conducted non-electrochemically.

29. A process according to claim 27 wherein said arene is a homocyclic arene.

30. A process according to claim 29 wherein said homocyclic arene is a fused ring arene.

31. A process according to claim 27 wherein said base is pyridine or a ring-substituted pyridine.

32. A process according to claim 27 wherein said arene is a homocyclic fused ring arene, and wherein said base is pyridine or a ring-substituted pyridine.

33. A process according to any of claims 1, 2, 3, 4, 5, 6, 7, 8, 9, 10, 11, 12, 13, 21, 22, 23, 24, 25, 26, 27, 28, 29, 30, 31, or 32 wherein the organic disulfide is a primary alkyl disulfide.

34. An adduct according to any of claims 14, 15, 16, 17, or 18 wherein the organothio group is a primary alkyl group.

35. A process which comprises subjecting dimethyl disulfide or diethyl sulfide to anodic oxidation in a solution formed from (i) an alkylthiatable arene containing only aromatic unsaturation, (ii) an organic electrochemical solvent, (iii) a dissolved supporting electrolyte, and optionally, (iv) an organic electrophilic base, such that a methylthiated or ethylthiated product is formed.

* * * * *